United States Patent
Grader et al.

(10) Patent No.: US 9,741,106 B2
(45) Date of Patent: Aug. 22, 2017

(54) COMPUTED TOMOGRAPHY (CT) SYSTEMS AND METHODS ANALYZING ROCK PROPERTY CHANGES RESULTING FROM A TREATMENT

(71) Applicant: Ingrain, Inc., Houston, TX (US)

(72) Inventors: Avrami Grader, Houston, TX (US); Chuck Baldwin, Houston, TX (US); Carl Sisk, Houston, TX (US)

(73) Assignee: INGRAIN, INC., Houston, TX (US)

( * ) Notice: Subject to any disclaimer, the term of this patent is extended or adjusted under 35 U.S.C. 154(b) by 44 days.

(21) Appl. No.: 14/038,376

(22) Filed: Sep. 26, 2013

(65) Prior Publication Data

US 2014/0086381 A1 Mar. 27, 2014

Related U.S. Application Data

(60) Provisional application No. 61/706,505, filed on Sep. 27, 2012.

(51) Int. Cl.
*G06T 7/00* (2017.01)
*G01N 23/04* (2006.01)
(Continued)

(52) U.S. Cl.
CPC ......... *G06T 7/0002* (2013.01); *G01N 23/046* (2013.01); *G01N 24/081* (2013.01);
(Continued)

(58) Field of Classification Search
CPC ........... G01N 2223/419; G01N 23/046; G01N 15/088; G01N 2015/0846;
(Continued)

(56) References Cited

U.S. PATENT DOCUMENTS

| 4,982,086 A | 1/1991 | Withjack |
| 8,068,579 B1 | 11/2011 | Yun et al. |

(Continued)

FOREIGN PATENT DOCUMENTS

| WO | 83/01509 | 4/1983 |
| WO | 2012/118868 | 9/2012 |
| WO | 2014/052665 | 4/2014 |

OTHER PUBLICATIONS

Grader et al., "Computations of Porosity and Permeability of Sparic Carbonate Using Multi-scale CT Images", 2009, International Symposium of the Society of Core Analysts, SCA2009-Temp Paper #03-10.*

(Continued)

*Primary Examiner* — Kenny Cese
(74) *Attorney, Agent, or Firm* — Iselin Law PLLC

(57) ABSTRACT

The effect of a treatment on a rock sample or sub-sample extracted from the rock sample can be analyzed through computed tomography (CT). To determine the effect of a treatment of a rock sample or the sub-sample, pre-treatment and post-treatment CT images of the rock sample or the sub-sample are captured. Further, the pre-treatment CT images and post-treatment CT images of the rock sample or the sub-sample are compared based on one or more alignment markers added to the rock sample or the sub-sample. In some embodiments, pre-treatment and post-treatment CT scans of an extracted sub-sample provide higher-resolution information regarding the effect of the treatment. Further, pre-treatment and post-treatment CT scans of a rock sample with a restored sub-sample may be considered and may provide additional information regarding the effect of the treatment on the rock sample or the sub-sample.

18 Claims, 5 Drawing Sheets

(51) Int. Cl.
*G01N 33/24* (2006.01)
*G01N 24/08* (2006.01)

(52) U.S. Cl.
CPC ........... *G01N 33/24* (2013.01); *G06T 7/0004* (2013.01); *G01N 2223/419* (2013.01); *G01N 2223/649* (2013.01); *G06T 2207/10081* (2013.01); *G06T 2207/30108* (2013.01)

(58) Field of Classification Search
CPC ....... G01N 2223/616; G01N 2223/649; G01N 21/87; G01N 33/24; G01N 33/381; G01N 24/081; G06T 2207/10081; G06T 2207/20221; G06T 7/0038; G06T 7/0004; G06T 2207/30181; G06T 7/11; G06T 7/0002
See application file for complete search history.

(56) References Cited

U.S. PATENT DOCUMENTS

| | | | |
|---|---|---|---|
| 8,155,377 | B2 | 4/2012 | Dvorkin et al. |
| 2009/0080705 | A1 | 3/2009 | Orpen |
| 2009/0259446 | A1 | 10/2009 | Zhang et al. |
| 2010/0135536 | A1 | 6/2010 | Dvorkin et al. |
| 2011/0004447 | A1 | 1/2011 | Hurley et al. |
| 2011/0004448 | A1 | 1/2011 | Hurley et al. |
| 2011/0181701 | A1* | 7/2011 | Varslot ............... G06T 7/30 348/46 |
| 2011/0295580 | A1 | 12/2011 | Sisk et al. |
| 2012/0197526 | A1* | 8/2012 | Leyte Guerrero ... G01N 15/088 702/2 |
| 2012/0275658 | A1 | 11/2012 | Hurley et al. |
| 2012/0277996 | A1* | 11/2012 | Hurley ............... G01V 99/005 702/11 |
| 2012/0281883 | A1 | 11/2012 | Hurley et al. |
| 2013/0028371 | A1 | 1/2013 | Derzhi |
| 2013/0073207 | A1 | 3/2013 | Ganz |
| 2013/0081882 | A1* | 4/2013 | Lin ..................... G01N 1/32 175/428 |
| 2013/0094716 | A1 | 4/2013 | Carpio et al. |

OTHER PUBLICATIONS

Grader et al., "Multi-scale Imaging Process for Computations of Porosity and Permeability on Carbonate Rocks".*

Papatzacos, Paul, "Cellular Automaton Model for Fluid Flow in Porous Media", Complex Systems 3 (1989), pp. 383-405, © Complex Systems Publication, Inc., Stavanger, Norway.

Liu, Jie et al., "Application of Percolation Theory to Microtomography of Structured Media: Percolation Threshold, Critical Exponents, and Upscaling", Physical Review E 83, 016106 (2011), 13 pgs, © American Physical Society, 1539-3755/2011/83(1)/016106(13).

Liu, Jie et al., "Improved Estimates of Percolation and Anisotropic Permeability From 3-D X-ray Microtomography Using Stochastic Analyses and Visualization", Geochemistry Geophysics Geosystems (G3), May 29, 2009, 13 pgs., vol. 10, No. 5, © American Geophysical Union (AGU) and the Geochemical Society, An Electronic Journal of the Earth Sciences.

Adalsteinsson, David et al., "Accurate and Efficient Implementation of Pore-Morphology-based Drainage Modeling in Two-dimensional Porous Media", Transport in Porous Media (2006) 65: 337-358, © Springer 2006, DOI 10.1007/s11242-005-6091-6.

Hazlett, R. D. "Simulation of Capillary-Dominated Displacements in Microtomographic Images of Reservoir Rocks", Transport in Porous Media 20: 21-35, 1995, © Kluwer Academic Publishers, The Netherlands.

Hilpert, Markus et al., "Pore-Morphology-Based Simulation of Drainage in Totally Wetting Porous Media", Advances in Water Resources 24 (2001), p. 243-255, © Elsevier Science Ltd.

Biswal, B. "Three-Dimensional Local Porosity Analysis of Porous Media", , Physica A 255 (1998), p. 221-241, © Elsevier Science Ltd.

Nur, Amos et al., "Effects of Carbon Dioxide Injection in Reactive Carbonates: Computational Rock Physics Basis for Time-Lapse Monitoring", Society of Petroleum Engineers, SPE-SAS-1186, May 15-18, 2011, 6 pgs.

Hilfer, R. "Review on Scale Dependent Characterization of the Microstructure of Porous Media", Transport in Porous Media 46: 373-390, 2002, © Kluwer Academic Publishers, The Netherlands.

PCT Search Report and Written Opinion, dated Mar. 5, 2014, Appl No. PCT/US2013/062034, "Computed Tomography (CT) Systems and Methods Analyzing Rock Property Changes Resulting from a Treatment," Filed Sep. 26, 2013, 13 pgs.

PCT International Preliminary Report on Patentability, dated Apr. 9, 2015, Appl No. PCT/US2013/062034, "Computed Tomography (CT) Systems and Methods Analyzing Rock Property Changes Resulting from a Treatment," Filed Sep. 26, 2013, 9 pgs.

GCC Examination Report, dated Oct. 25, 2016, Appl No. 25457, "Computed Tomography (CT) Systems and Methods Analyzing Rock Property Changes Resulting from a Treatment," Filed Sep. 29, 2013, 4 pgs.

* cited by examiner

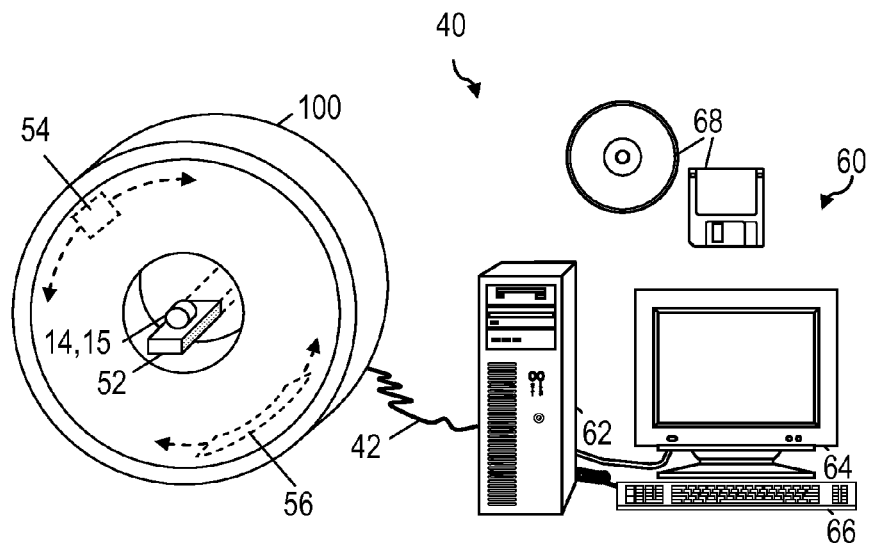
FIG. 2
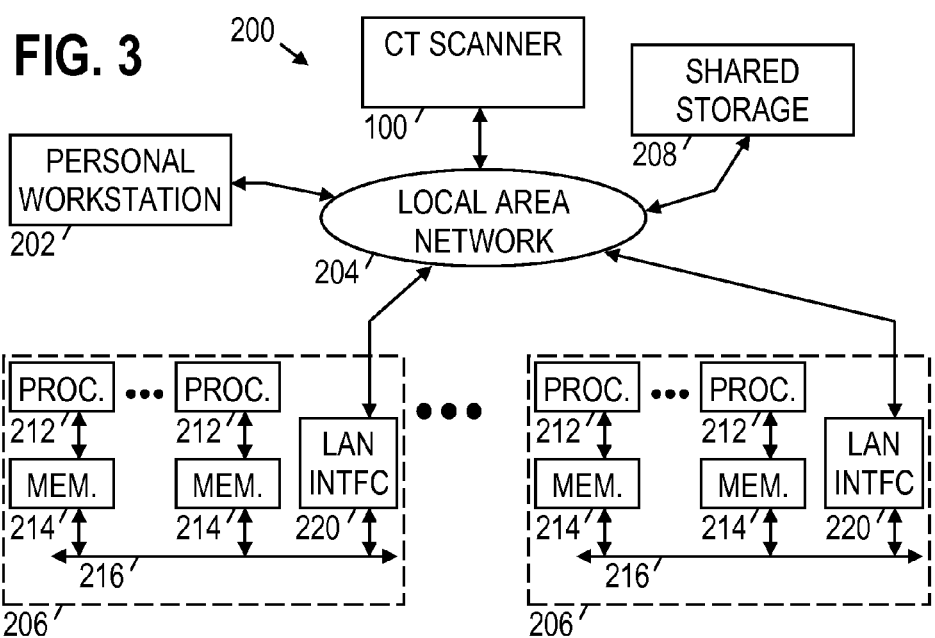

COMPUTED TOMOGRAPHY (CT) SYSTEMS AND METHODS ANALYZING ROCK PROPERTY CHANGES RESULTING FROM A TREATMENT

CROSS-REFERENCE TO RELATED APPLICATIONS

This application claims priority to Provisional U.S. Application Ser. No. 61/706,505, titled "Computed Tomography (CT) Systems and Methods Analyzing Rock Property Changes Resulting from a Treatment" and filed Sep. 27, 2012 by Avrami Grader, Chuck Baldwin, and Carl Sisk, which is incorporated herein by reference.

BACKGROUND

Microscopy offers scientists and engineers a way to gain a better understanding of the materials with which they work. Under high magnification, it becomes evident that many materials (including rock and bone) have a porous microstructure that permits fluid flows. Such fluid flows are often of great interest, e.g., in subterranean hydrocarbon reservoirs. Accordingly, significant efforts have been expended to characterize materials in terms of their flow-related properties including porosity, permeability, and the relation between the two.

Scientists typically characterize materials in the laboratory by applying selected fluids with a range of pressure differentials across the sample. Such injection tests often require weeks and are fraught with difficulties, including requirements for high temperatures, pressures, and fluid volumes, risks of leakage and equipment failure, and imprecise initial conditions. (Flow-related measurements are generally dependent not only on the applied fluids and pressures, but also on the history of the sample. Experiments should begin with the sample in a native state, but this state is difficult to achieve once the sample has been removed from its original environment.)

Accordingly, industry has turned to digital rock analysis to characterize the flow-related properties of materials in a fast, safe, and repeatable fashion. Efforts to increase the amount of information that can be derived from digital rock analysis are ongoing.

BRIEF DESCRIPTION OF THE DRAWINGS

Accordingly, there are disclosed herein computed tomography (CT) systems and methods that determine rock property changes resulting from a treatment. In the drawings:

FIG. 2 shows an illustrative CT system.

FIG. 3 shows an illustrative high performance computing network.

Figure 1:
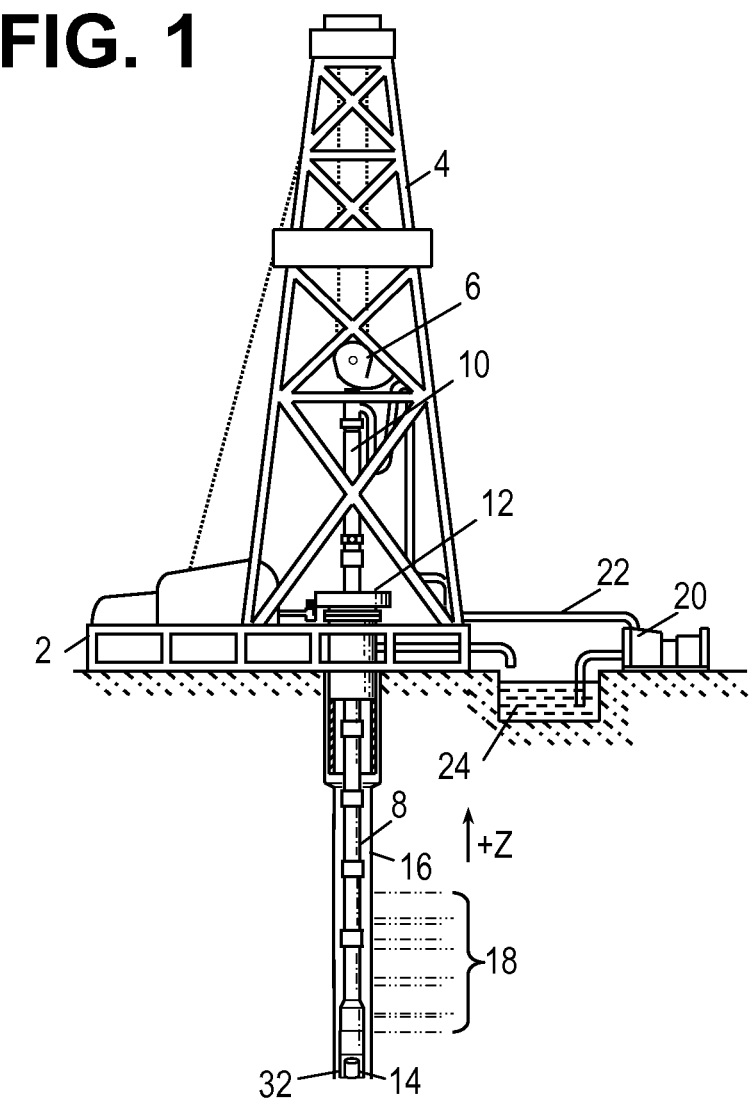
FIG. 1 shows an illustrative drilling environment.

It should be understood, however, that the specific embodiments given in the drawings and detailed description below do not limit the disclosure. On the contrary, they provide the foundation for one of ordinary skill to discern the alternative forms, equivalents, and other modifications that are encompassed in the scope of the appended claims.

DETAILED DESCRIPTION

Disclosed herein are methods and systems for applying computed tomography (CT) analysis to improve understanding of the effects of treatment on rock core samples (plugs) or sub-samples. The rock core samples or sub-samples described herein may vary in size and may be obtained using known drilling techniques. The size of the rock core samples or sub-samples should be adequate to facilitate treatment as well as physical tests for determining properties of the rock samples or sub-samples such as porosity, permeability, and seismic velocity. Before and after a rock sample or sub-sample is treated, CT scanning of the rock core sample or sub-sample is performed. Without limitation to other examples, a suitable rock core sample may be approximately cylindrical with a radius of 10-20 mm and a length of 50-60 mm. Meanwhile, without limitation to other examples, sub-samples may be approximately cylindrical with a radius of 2-4 mm and a length of 5-10 mm.

As disclosed herein, image capture and digital rock physics (DRP) analysis may be applied to rock samples and sub-subsamples to determine rock properties such as porosity, permeability, and seismic velocity. However, if the porosity of a rock sample is not detectable by whole plug scanning, then one or more sub-samples are then extracted from the rock sample and scanned at a higher resolution to reveal a detectable porosity structure. Accordingly, extracting a sub-sample from a rock sample and capturing pre-treatment and post-treatment CT images of the sub-sample may be in response to determining that detectable porosity in at least one CT image of the rock sample is less than a threshold level (i.e., a higher resolution is needed to determine rock properties such as porosity, permeability, and seismic velocity).

In at least some embodiments, a sub-sample may subsequently be restored to its parent sample to enable standard physical tests and treatment on the parent sample and any related sub-samples. Alternatively, treatments and physical tests may be applied to a sub-sample while separated from its parent sample. After completion of a treatment, physical tests may be performed on rock samples (or sub-samples) to ascertain the effect of the treatments. Further, CT scanning of a parent sample and any sub-samples are performed again (the sub-samples may be removed again as needed) to enable an image-based comparison of a rock sample or sub-sample before and after the treatments. When analyzing the pre-treatment and post-treatment CT scans, image normalization operations (to normalize orientation, scaling, or color) may be performed. The results of comparing pre-treatment and post-treatment CT images may be recorded as a report that describes the effects of a treatment on a rock core sample (including any sub-samples). The report may include charts, histograms, joint histograms, distribution of changes between pre-treatment 2D/3D images and post-treatment 2D/3D images, segmented images, or other analysis comparison of pre-treatment and post-treatment CT images. Further, the report may relate pre-treatment CT image features or post-treatment CT image features with physical test parameters (pre-treatment or post-treatment) and/or with DRP parameters (pre-treatment or post-treatment). The report may include pre-treatment information or post-treatment information in various forms as described herein.

It should be understood that the treatments described herein may vary. Some treatments may be intended to increase permeability or porosity of a rock sample, while others are intended to decrease permeability or porosity of a rock sample. Further, some treatments may be carried out to test a particular treatment application technique. Further, some treatments are requested or performed by entities that do not know what the effect of the treatment on the rock sample will be.

Various operations are described herein such as pre-treatment CT scanning, pre-treatment physical tests, treatment, post-treatment physical tests, post-treatment CT scanning, and analysis of pre-treatment and post-treatment CT images. These various operations may be performed by the same entity or different entities. As an example and without limitation to other scenarios, CT scanning/analysis of samples and sub-samples may be performed by one entity as a service to at least one other entity interested in collecting information regarding the effect of treatments on a rock sample.

Without limitation to other drilling arrangements, FIG. 1 shows an illustrative 1 drilling environment. As shown, a drilling platform 2 supports a derrick 4 having a traveling block 6 for raising and lowering a drill string 8. A kelly 10 supports the drill string 8 as it is lowered through a rotary table 12. A drill bit 32 is driven by a downhole motor and/or rotation of the drill string 8. As bit 32 rotates, it creates a borehole 16 that passes through various formations 18. In some drilling scenarios, a pump 20 circulates drilling fluid through a feed pipe 22 to kelly 10, downhole through the interior of drill string 8, through orifices in drill bit 32, back to the surface via the annulus around drill string 8, and into a retention pit 24. The drilling fluid transports cuttings from the borehole into the pit 24 and aids in maintaining the borehole integrity.

In addition to producing cuttings, the drill bit 32 also may collect a rock core sample 14 for later analysis as described herein. In various embodiments, downhole cutting tools such as drill bit 32 may collect rock core samples from any of the formations 18 along borehole 16 for later analysis. Additionally, cutting tools such as the drill bit 32 (or supplemental cutting tools along drill string 8) may extend in different directions (e.g., angled or horizontal) along the borehole 16 to collect sidewall core rock samples. The process of drilling for rock core samples may occur while the borehole 16 is being drilled or afterwards. More generally speaking, the rock core sample 14 may correspond to sidewall cores, whole cores, drill cuttings, outcrop quarrying samples, or other sample sources which can provide suitable samples for analysis using methods of the present disclosure.

FIG. 2 provides an illustration of a CT system 40. As shown, a computer 60 is coupled via communication line 42 to a CT scanner 100. The CT scanner 100 has a platform 52 (for holding a rock sample 14 or sub-sample 15), an X-ray source 54, and an X-ray detector 56. The X-ray source 54 and the X-ray detector 56 may rotate as shown. Alternatively, the X-ray source 54 may rotate while the X-ray detector 56 is stationary. Without limitation to other embodiments, the CT scanner 100 may correspond to a $4^{th}$ generation CT scanner. Although not required, different CT scanners may be used for scanning rock samples and sub-samples as described herein.

X-ray signals captured by the CT scanner 100 may be stored and processed by the computer 60 to generate CT images (e.g., of rock sample 14 or sub-sample 15). The computer 60 also may provide one or more control signals (automatically or by user request) to initiate CT scanning operations. The illustrated computer 60 includes a chassis 62, an output device 64 (e.g., a monitor as shown in FIG. 1, or a printer), an input device 66 (e.g., a keyboard), and information storage media 68 (e.g., magnetic or optical data storage disks). The information storage media 68 may be employed to provide CT scanning instructions, CT data storage, CT image analysis software, etc. The computer 60 may be implemented in different forms including, e.g., an embedded computer permanently installed as part of the CT scanner 100, a portable computer that is plugged into the CT scanner 100 as desired to collect data, a remote desktop computer coupled to the CT scanner 100 via a wireless link and/or a wired computer network, a mobile phone/PDA, or indeed any electronic device having a programmable processor and an interface for I/O.

As previously mentioned, the information storage media 68 may store a software program for execution by computer 60. For example, instructions of a software program may cause the computer 60 to collect data/images from CT scanner operations. Further, instructions of a software program may cause the computer 60 to normalize pre-treatment and post-treatment CT images. Further, instructions of a software program may cause the computer 60 to analyze/compare pre-treatment and post-treatment CT images as described herein. Further, instructions of a software program may cause the computer 60 to correlate variations in pre-treatment and post-treatment permeability, porosity, or seismic velocity of a rock sample with pre-treatment and post-treatment CT images. Various types of analysis are possible based on pre-treatment and post-treatment CT images, pre-treatment and post-treatment physical test data, and DRP data. The analysis of the data available from CT scanning, physical tests, and DRP analysis may result in generating charts to display information regarding a rock sample or sub-sample such as: pre-treatment porosity versus post-treatment porosity; pre-treatment permeability versus post-treatment permeability; formation factor versus porosity; pre-treatment porosity/permeability versus post-treatment porosity/permeability; pre-treatment velocity/porosity versus post-treatment velocity/porosity; pre-treatment compressional velocity versus post-treatment compressional velocity; pre-treatment shear velocity versus post-treatment shear velocity; correlation studies of pre-treatment/post-treatment porosity, pre-treatment/post-treatment permeability, or pre-treatment/post-treatment velocity; histograms based on pre-treatment/post-treatment porosity, pre-treatment/post-treatment permeability, or pre-treatment/post-treatment velocity; and profiles of average CT values as a function of depth for pre-treatment CT images and post-treatment CT images. Select pre-treatment CT images and post-treatment CT images as well as select charts may be included in a report. The report may be generated, for example, according to customer specifications for information and/or to highlight notable changes in a rock sample or sub-sample that has undergone a treatment. Further, the report may include joint histograms, distribution of changes between pre-treatment 2D/3D images and post-treatment 2D/3D images, segmented images. The report may include pre-treatment information or post-treatment information in various forms as described herein.

FIG. 3 is an example of a larger system 200 within which the CT scanner 100 can be employed. In the larger system 200, a personal workstation 202 is coupled to the CT scanner 100 by a local area network (LAN) 204. The LAN 204 further enables intercommunication between the CT scanner 100, personal workstation 202, one or more high performance computing platforms 206, and one or more shared storage devices 208 (such as a RAID, NAS, SAN, or the like). The high performance computing platform 206 generally employs multiple processors 212 each coupled to a local memory 214. An internal bus 216 provides high bandwidth communication between the multiple processors (via the local memories) and a network interface 220. Parallel processing software resident in the memories 214 enables the multiple processors to cooperatively break down and execute the tasks to be performed in an expedited fashion, accessing the shared storage device 208 as needed to deliver results and/or to obtain the input data and intermediate results.

Typically, a user would employ a personal workstation 202 (such as a desktop or laptop computer) to interact with the larger system 200. Software in the memory of the personal workstation 202 causes its one or more processors to interact with the user via a user interface, enabling the user to, e.g., craft and execute software for processing the images acquired by the CT scanner 100. For tasks having small computational demands, the software may be executed on the personal workstation 202, whereas computationally demanding tasks may be preferentially run on the high performance computing platform 206.

Figure 4:
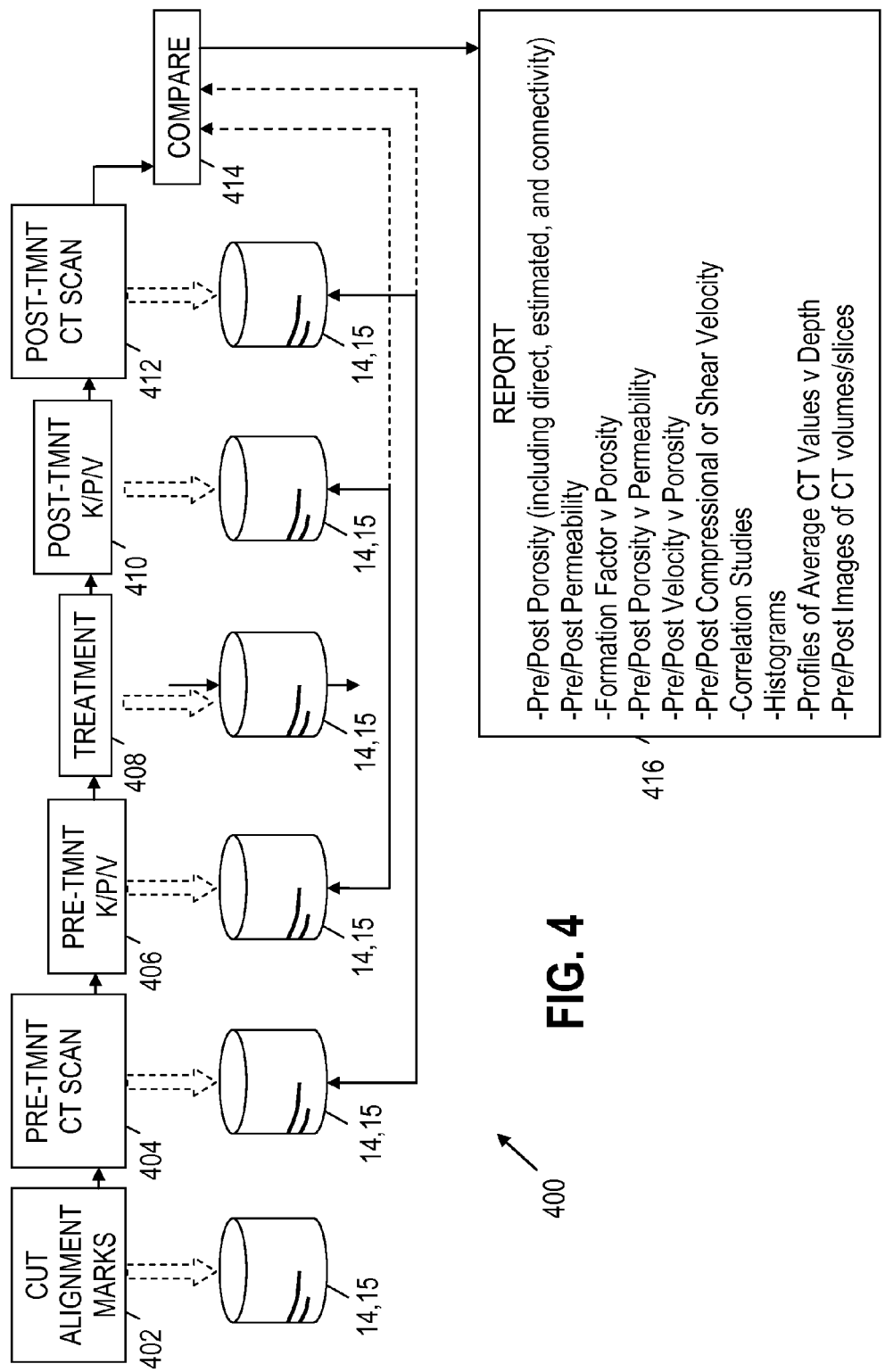
FIG. 4 shows an illustrative process for CT analysis of a rock core sample or sub-sample before and after a treatment.

FIG. 4 shows an illustrative process 400 for CT analysis of a rock core sample 14 or sub-sample 15 before and after a treatment. During the process 400, a rock sample 14 or sub-sample 15 is subjected to various stages. The dashed block arrows in FIG. 4 are for convenience only to show the progression of a rock sample 14 or sub-sample 15 through the various stages. First, alignment marks are cut in the rock sample 14 or sub-sample 15 at block 402. The alignment marks may comprise two marks as shown, where one mark is longer than the other, both marks sharing a common starting point on the sample's circumference to make the mark pattern asymmetric and distinctive. In some embodiments, the alignments marks are shallow cuts that extend around part of the rock sample perimeter as is shown. Although not required, the alignment marks shown for process 400 are oriented horizontally and in a direction that is substantially perpendicular to the direction of fluid flow for the treatment of block 408. In alternative embodiments, one or more shallow alignment marks may be oriented vertically and in a direction that is substantially parallel to the direction of fluid flow for the treatment of block 408. In either case, the alignments marks should not interrupt and should not be affected by the treatment of block 408. To decrease the effect of the alignment marks on the treatment of block 408, epoxy or another hardening adhesive may be applied to fill in the alignment marks. In such case, the alignment marks are still visible in the pre-treatment and post-treatment CT scans and can be used to align or scale images as needed for analysis.

Additionally or alternatively, other alignment marks that do not interfere (or minimally interfere) with treatment or physical tests may be added to rock sample 14 or sub-sample 15. For example, a material visible in CT scans may be added to rock sample 14 or sub-sample 15 to provide alignment marks. Further, pattern recognition software may be used to identify unique pattern characteristics of rock sample 14 or sub-sample 15 that enable alignment. As an example, the pattern recognition software may identify shapes, lines, or other unique marks in CT images. To align CT images (e.g., pre-treatment and post-treatment images), unique marks, patterns, or templates are compared to determine whether a match occurs. The orientation/size of unique marks, patterns, marker materials, or cuts in rock sample 14 or sub-sample 15 can also be used as input parameters for CT image rotation/scaling operations. The alignment and comparison of CT images using natural or man-made markers enables a treatment's effect on porosity or other rock attributes to be analyzed, charted, and reported as described herein.

At block 404, a pre-treatment CT scan of the rock sample 14 or sub-sample 15 is performed by a CT scanner. At block 406, pre-treatment physical rock property and fabric test parameters such as permeability ("K"), porosity ("P"), and seismic velocity ("V") are determined for the rock sample. At block 408, treatment is applied to the rock sample 14 or sub-sample 15. At block 410, various post-treatment physical test parameters such as changes in distribution of properties and changes in rock fabric, K, P, or V are determined for the rock sample 14 or sub-sample 15. Post-treatment CT scanning is performed on the rock sample 14 or sub-sample 15 at block 412. At block 414, a comparison is performed to compare pre-treatment CT images with post-treatment CT images and/or to correlate CT images with pre-treatment K/P/V parameters or post-treatment K/P/V parameters. At block 416, a report is generated. Without limitation to other examples, the report of block 416 may report on: pre-treatment rock properties/fabric vs post-treatment rock properties/fabric; pre-treatment porosity versus post-treatment porosity; pre-treatment permeability versus post-treatment permeability; formation factor versus porosity; pre-treatment porosity/permeability versus post-treatment porosity/permeability; pre-treatment velocity/porosity versus post-treatment velocity/porosity; pre-treatment compressional velocity versus post-treatment compressional velocity; pre-treatment shear velocity versus post-treatment shear velocity; correlation studies of pre/post porosity, pre/post permeability, or pre/post velocity; histograms based on pre/post porosity, pre/post permeability, or pre/post velocity; and profiles of average CT values as a function of depth for pre-treatment CT images and post-treatment CT images. Further, the report of block 416 may include select pre-treatment CT images and post-treatment CT images. The information in the report of block 416 may be based on customer-specified criteria and/or notable changes identified by comparison of pre-treatment CT images with post-treatment CT images.

Figure 5:
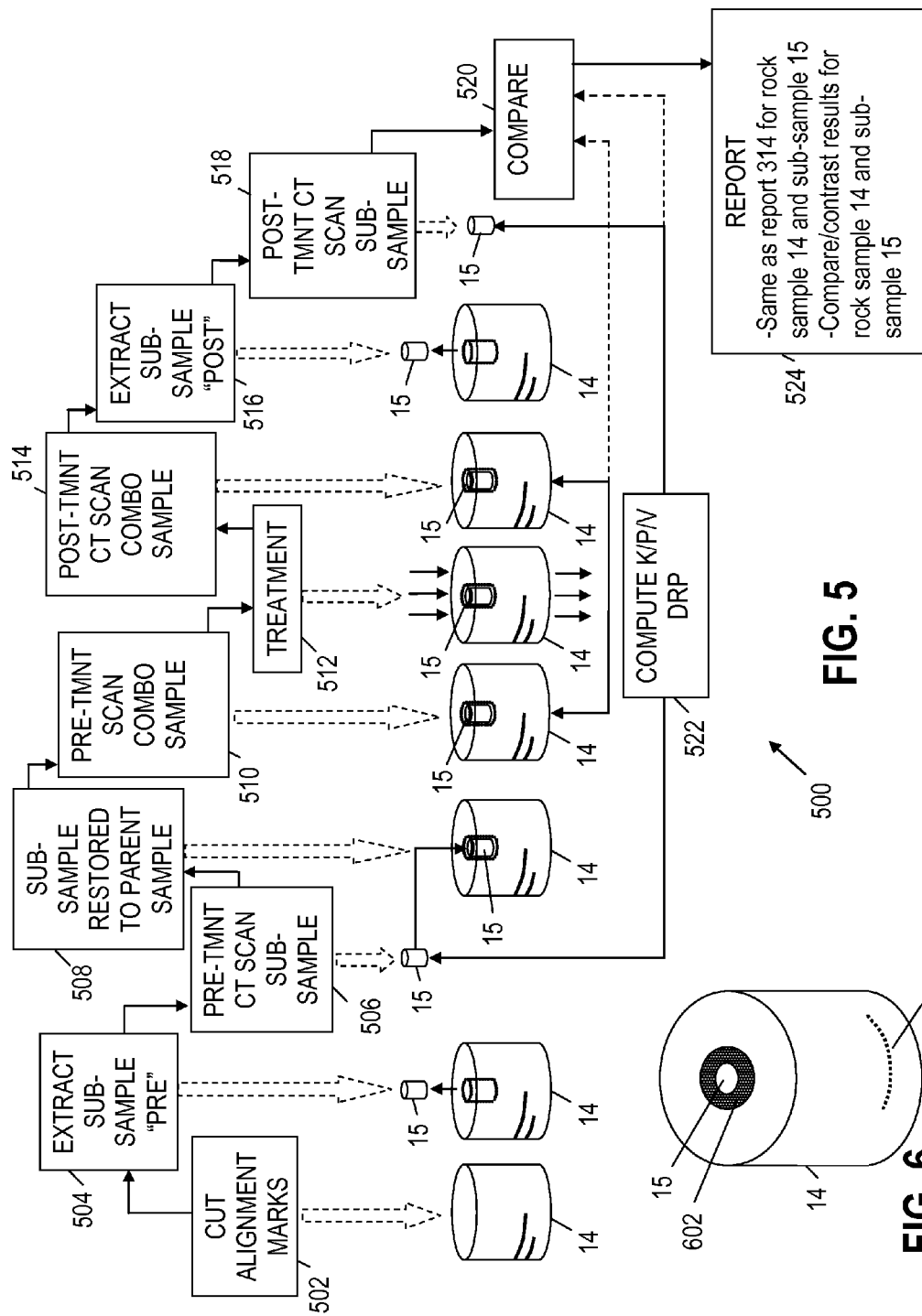
FIG. 5 shows an illustrative process for CT analysis of a rock core sample and related sub-sample before and after a treatment.

FIG. 5 shows an illustrative process 500 for CT analysis of rock sample 14 and sub-sample 15 before and after a treatment. During the process 500, the rock sample 14 and sub-sample 15 are subjected to various stages. The dashed block arrows in FIG. 5 are for convenience only to show the progression of the rock sample 14 and sub-sample 15 through the various stages. First, alignment marks are cut in the rock sample 14 at block 502. The alignment marks of block 502 may correspond to the mark options discussed for block 402 of FIG. 4. At block 504, sub-sample 15 is extracted from the rock sample 14 before treatment, and pre-treatment CT scanning of the sub-sample 15 is performed at block 506. At block 508, the sub-sample 15 is inserted into (restored to) the rock sample 14 before treatment.

Figure 6:
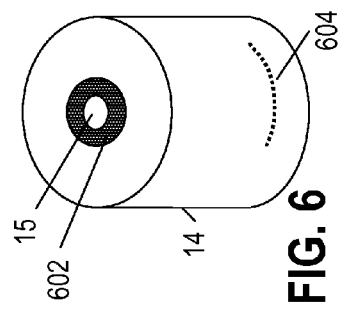
FIG. 6 shows an illustrative rock core sample and sub-sample related to the method of FIG. 5.

FIG. 6 shows rock sample 14 and sub-sample 15 after the insertion step of block 508. As shown, the rock sample 14 has one or more alignment marks 604 added or identified (e.g., with pattern recognition software) at step 502. In addition, a sub-sample 15 was previously extracted at block 504 for CT scanning as in block 506. As an example, a drilling tool may be employed to drill around and break off the sub-sample 15. After CT scanning, the sub-sample 15 has been inserted into its place in the rock sample 14 at step 508. For step 508, an adhesive such as epoxy may be employed to affix the sub-sample 15 in its original place in rock sample 14. Further, if the sub-sample 15 is broken off from rock sample 14 during the extraction step of block 504, a rough surface remains on both the sub-sample 15 and the rock sample 14 that facilitates restoring the sub-sample 15 to rock sample 14 at block 508 (i.e., the sub-sample usually only fits well when properly aligned). Although only one sub-sample 15 is shown for rock sample 14, it should be understood that additional sub-samples (e.g., 2, 3, or more sub-samples) may be extracted from, CT scanned, and restored to a parent sample as described herein. The sub-samples may be extracted from the top, bottom, or sides of a parent core. Extraction steps, restoration steps, and subsequent extraction steps may be performed for sub-samples as part of pre-treatment analysis and post-treatment analysis regardless of whether sub-samples are extracted from the top, bottom, or sides of a parent core.

In some embodiments, CT scanning or other imaging technology may be employed to verify that the restoration of a sub-sample to its parent sample is successful. To be successful, the restoration should enable physical tests and/or treatment of the parent sample and its sub-sample(s). CT scanning may reveal, for example, the accumulation of adhesive material between a sub-sample and its parent sample in the direction of fluid flow for treatment. In such case, a sub-sample may be extracted and restored again until the restoration process is determined to be successful.

At block 510, CT scanning of the rock sample 14 with the restored sub-sample 15 is performed. Subsequently, treatment of the rock sample 14 with the restored sub-sample 15 is performed at block 512. At block 514, post-treatment CT scanning of the rock sample 14 with the restored sub-sample 15 is performed. At block 516, the sub-sample 15 is again extracted from the rock sample 14, after which the extracted sub-sample 15 is subjected to post-treatment CT scanning at block 518. At block 520, the pre-treatment and post-treatment CT scans of the rock sample 14 with the restored sub-sample 15 are compared. Further, the pre-treatment and post-treatment CT scans of the sub-sample 15 may be compared at block 520. Further, pre-treatment and post-treatment DRP-based parameters (e.g., K, P, V) for the sub-sample 15 may be compared at block 520. The comparisons of block 520 may be based on previous alignment operations, previous extraction operations to produce pre-treatment and post-treatment digital volumes that correspond to a physical volume, previous scaling operations, or previous color calibration operations. At the comparison step of block 520, CT images are correlated with each other, and may be correlated with physical test parameters or DRP-based parameters.

The pre-treatment and post-treatment DRP-based parameters for the sub-sample 15 may be determined at block 522. The comparisons of block 520 may be based on various computer programs that operate to align, scale, or color calibrate CT images, to correlate CT images with each other, and to correlate CT images with physical test parameters or DRP-based parameters.

The result of the comparisons of block 520 is a report 524, which may include the same or similar information as was described for the report 416 of FIG. 4. In addition, the report 524 may compare and contrast the results of CT scans of the rock sample 14 with CT scans of the sub-sample 15.

In some embodiments, processes 400 and 500 are combined. In other words, pre-treatment and post-treatment CT scans may be obtained for rock sample 14, sub-sample 15, or a combination sample (rock sample 14 with restored sub-sample 15) as described herein. Further, pre-treatment and post-treatment physical tests as described for steps 406 and 410 of process 400 as well as DRP analysis as described for step 522 may be employed to gather information that is correlated with pre-treatment and post-treatment CT images to generate a report regarding the effect of treatment on rock sample 14, sub-sample 15, or a combination sample (rock sample 14 with restored sub-sample 15).

Figure 7:
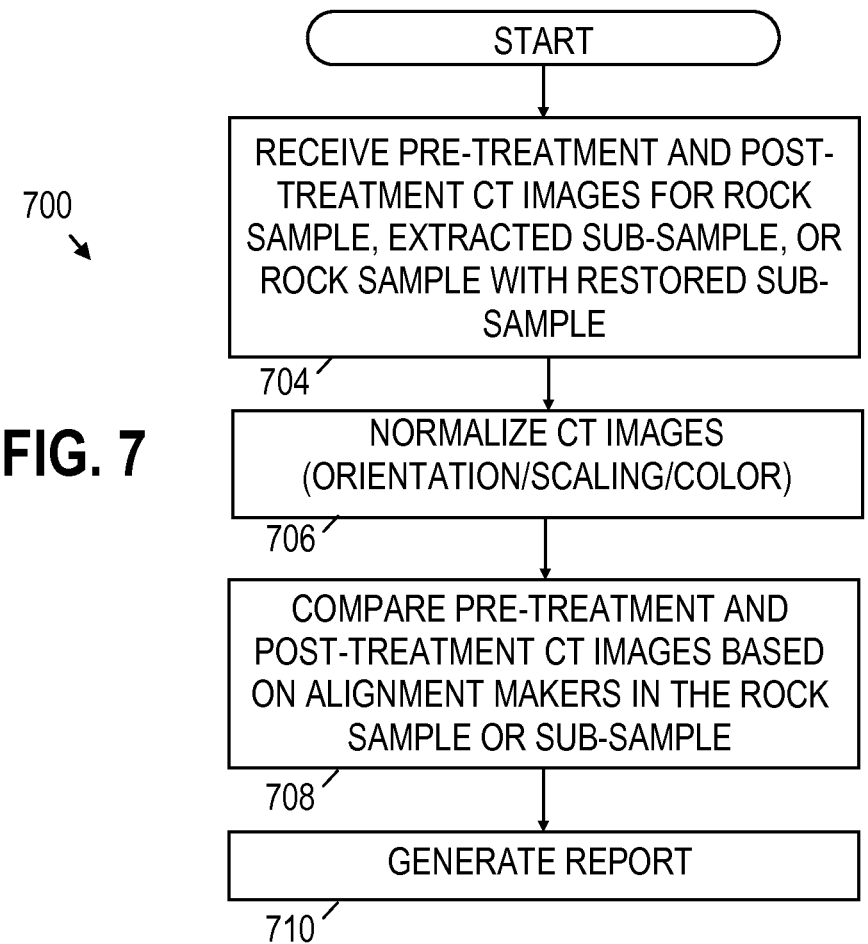
FIG. 7 is a flowchart of an illustrative CT analysis method.

FIG. 7 is a flowchart of an illustrative CT analysis method 700. The method 700 may be performed by a computer system such as computer 60 or computer platform 206. As shown, the method 700 starts by receiving pre-treatment CT images and post-treatment CT images for a rock sample, an extracted sub-sample, or a rock sample with a restored sub-sample (block 704). The CT images are normalized at block 706. For example, the orientation, scaling, or color of pre-treatment and post-treatment CT images may be normalized. Without limitation to other comparisons, pre/post treatment CT images of a rock sample may be normalized for comparison with other pre/post CT images of the rock sample, pre/post treatment CT images of an extracted sub-sample may be normalized for comparison with other pre/post treatment CT images of the extracted sub-sample, and/or pre/post treatment CT images of rock sample with a restored sub-sample may normalized for comparison with other pre/post treatment CT images of the rock sample with the restored sub-sample). At block 708, pre-treatment CT images and post-treatment CT images are compared based on alignment markers added to or otherwise identified in the rock sample or the sub-sample as described herein. A report is generated at block 710 to describe the effect of the treatment on the rock sample, the extracted sub-sample, or the rock sample with restored sub-sample corresponding to the received pre-treatment and post-treatment CT images. The report may include words, images, charts, graphs, physical test parameters, and/or DRP-based parameters as described herein to explain the effect of a treatment on a rock sample, an extracted sub-sample, or a rock sample with a restored sub-sample.

For explanatory purposes, the operations of the foregoing processes and method have been described as occurring in an ordered, sequential manner, but it should be understood that at least some of the operations can occur in a different order, in parallel, and/or in an asynchronous manner.

Numerous variations and modifications will become apparent to those skilled in the art once the above disclosure is fully appreciated. In some embodiments, pre-treatment CT scanning operations, treatment operations, post-treatment CT scanning operations, and CT image analysis are performed by a single entity. Alternatively, one of more of the pre-treatment CT scanning operations, treatment operations, post-treatment CT scanning operations, and CT image analysis operations described herein may be performed by different entities.

It is intended that the following claims be interpreted to embrace all such variations and modifications.

What is claimed is:

1. A method that comprises:
   capturing pre-treatment computed tomography (CT) images of a rock sample comprising at least one sub-sample portion and a remainder portion, wherein the pre-treatment CT images are captured while the at least one sub-sample portion and the remainder portion are physically separated;
   capturing post-treatment CT images of the at least one sub-sample portion and the remainder portion while physically separated, wherein the treatment comprises a permeability or porosity adjustment treatment that is applied while the at least one sub-sample portion and the remainder portion are rejoined together;

comparing at least some of the pre-treatment CT images with respective post-treatment CT images; and generating a report that describes the treatment's effect based on said comparison.

2. The method of claim 1, further comprising adding alignment markers to each of the at least one sub-sample portion, wherein said alignment markers comprise two marks having different lengths cut or added along an outer surface of each sub-sample portion, and wherein said marks do not interfere with fluid flow for the treatment.

3. The method of claim 1, further comprising receiving pre-treatment and post-treatment physical parameters for the at least one sub-sample portion or the remainder portion, and correlating pre-treatment CT image features and post-treatment CT image features with the pre-treatment and post-treatment physical parameters, wherein the report is based in part on said correlating.

4. The method of claim 1, further comprising receiving pre-treatment and post-treatment digital rock physics (DRP) parameters associated with the at least one sub-sample portion or the remainder portion, and correlating pre-treatment CT image features and post-treatment CT image features with said pre-treatment and post-treatment DRP parameters, wherein the report is based in part on said correlating.

5. The method of claim 1, wherein generating the report comprises profiling an average CT value as a function of depth for the pre-treatment CT images and post-treatment CT images.

6. The method of claim 1, further comprising rejoining together the at least one sub-sample potion and the remainder portion using adhesive to maintain a predetermined position of the at least one sub-sample portion relative to the remainder portion.

7. The method of claim 1, wherein the at least one sub-sample portion comprises a plurality of sub-sample portions corresponding to different sides of the rock sample, and wherein the report describes an effect of the treatment on the plurality of sub-sample portions.

8. A system that comprises:
a memory having software; and
one or more processors coupled to the memory to execute the software, the software causing the one or more processors to:
receive pre-treatment computed tomography (CT) images of a rock sample comprising at least one sub-sample portion and a remainder portion, wherein the pre-treatment CT images are captured while the at least one sub-sample portion and the remainder portion are physically separated;
receive post-treatment CT images of the at least one sub-sample portion and the remainder portion, wherein the post-treatment CT images are captured while the at least one sub-sample portion and the remainder portion are physically separated, wherein the treatment comprises a permeability or porosity adjustment treatment that is applied while the at least one sub-sample portion and the remainder portion are rejoined together;
compare at least some of the pre-treatment CT images with respective post-treatment CT images; and
generate a report that describes the treatment's effect based on the comparison.

9. The system of claim 8, wherein the software further causes the one or more processors to align pre-treatment CT images and post-treatment CT based on alignment markers identified for each of the at least one sub-sample potion.

10. The system of claim 8, wherein the software further causes the one or more processors to receive pre-treatment and post-treatment physical test parameters for the at least one sub-sample portion or the remainder portion, and to correlate pre-treatment CT image features and post-treatment CT image features with said pre-treatment and post-treatment physical test parameters.

11. The system of claim 8, wherein the software further causes the one or more processors to receive pre-treatment and post-treatment digital rock physics (DRP) parameters associated with the at least one sub-sample portion or the remainder portion, and to correlate pre-treatment CT image features and post-treatment CT image features with said pre-treatment and post-treatment DRP parameters.

12. The system of claim 8, wherein the software further causes the one or more processors to receive pre-treatment and post-treatment physical parameters for the at least one sub-sample portion or the remainder portion, and to correlate pre-treatment CT image features and post-treatment CT image features with the pre-treatment and post-treatment physical parameters, wherein the report is based in part on the correlation.

13. The system of claim 8, wherein the software further further causes the one or more processors to receive pre-treatment and post-treatment digital rock physics (DRP) parameters associated with the at least one sub-sample portion or the remainder portion, and to correlate pre-treatment CT image features and post-treatment CT image features with said pre-treatment and post-treatment DRP parameters, wherein the report is based in part on the correlation.

14. The system of claim 8, wherein the software causes the one or more processors to generate the report by profiling an average CT value as a function of depth for the pre-treatment CT images and post-treatment CT images.

15. A non-transitory computer-readable medium storing software that, when executed, causes one or more processors to:
receive pre-treatment computed tomography (CT) images of a rock sample comprising at least one sub-sample portion and a remainder portion, wherein the pre-treatment CT images are captured while the at least one sub-sample portion and the remainder portion are physically separated;
receive post-treatment CT images of the at least one sub-sample portion and the remainder portion, wherein the pre-treatment CT images are captured while the at least one sub-sample portion and the remainder portion are physically separated, and wherein the treatment comprises a permeability or porosity adjustment treatment that is performed while the at least one sub-sample portion and the remainder portion are rejoined together;
compare at least some of the pre-treatment CT images with respective post-treatment CT images; and
generate a report that describes a treatment's effect based on the comparison.

16. The non-transitory computer-readable medium of claim 15, wherein the software further causes the one or more processors to receive pre-treatment and post-treatment physical parameters for the at least one sub-sample portion or the remainder portion, and to correlate pre-treatment CT image features and post-treatment CT image features with the pre-treatment and post-treatment physical parameters, wherein the report is based in part on the correlation.

17. The non-transitory computer-readable medium of claim 15, wherein the software further further causes the one or more processors to receive pre-treatment and post-treatment digital rock physics (DRP) parameters associated with the at least one sub-sample portion or the remainder portion, and to correlate pre-treatment CT image features and post-treatment CT image features with said pre-treatment and post-treatment DRP parameters, wherein the report is based in part on the correlation.

18. The non-transitory computer-readable medium of claim 15, wherein the software causes the one or more processors to generate the report by profiling an average CT value as a function of depth for the pre-treatment CT images and post-treatment CT images.

* * * * *